(12) United States Patent
Goldberger et al.

(10) Patent No.: US 8,092,385 B2
(45) Date of Patent: Jan. 10, 2012

(54) FLUID ACCESS INTERFACE

(75) Inventors: Daniel Goldberger, Boulder, CO (US); Eric Shreve, Louisville, CO (US); Wayne Siebrecht, Golden, CO (US); Benny Pesach, Rosh Ha'ayin (IL); Gidi Pesach, Kafar Vitikin (IL); Gabby Bitton, Jerusalem (IL); Ron Nagar, Tel Aviv (IL); Dalia Argaman, Hod-Hasharon (IL); Stephen Bellomo, Zirchron Yaacov (IL); Robert Larson, Salt Lake City, UT (US); Larry Johnson, Bennett, CO (US); Jill Klomhaus, Longmont, CO (US)

(73) Assignee: IntelliDx, Inc., Santa Clara ( * ) Notice: Subject to any disclaimer, the term of this patent is extended or adjusted under 35 U.S.C. 154(b) by 1542 days.

(21) Appl. No.: 11/419,784

(22) Filed: May 23, 2006

(65) Prior Publication Data

US 2008/0275324 A1    Nov. 6, 2008

(51) Int. Cl.
*A61B 5/00* (2006.01)
(52) U.S. Cl. .................... 600/365; 600/309; 600/575
(58) Field of Classification Search .................. 600/345, 600/347, 365, 575; 604/6.11, 6.12
See application file for complete search history.

(56) References Cited

U.S. PATENT DOCUMENTS

| | | | |
|---|---|---|---|
| 2,483,924 A | 10/1949 | Mouliner | |
| 3,340,869 A | 9/1967 | Bane | |
| 3,469,577 A | 9/1969 | Kater | |
| 3,498,899 A | 3/1970 | Kater et al. | |
| 3,539,300 A | 11/1970 | Stone | |
| 3,910,256 A | 10/1975 | Clark et al. | |
| 3,993,049 A | 11/1976 | Kater | |
| 4,077,395 A | 3/1978 | Woolner | |
| 4,094,822 A | 6/1978 | Kater | |
| 4,127,111 A | 11/1978 | Drolet | |
| 4,218,421 A | 8/1980 | Mack, Jr. et al. | |
| 4,240,438 A * | 12/1980 | Updike et al. | 600/347 |
| 4,258,717 A | 3/1981 | Bisera et al. | |
| 4,340,457 A | 7/1982 | Kater | |
| 4,411,792 A | 10/1983 | Babb | |
| 4,535,786 A | 8/1985 | Kater | |
| 4,573,968 A * | 3/1986 | Parker | 604/67 |
| 4,608,996 A | 9/1986 | Brown | |
| 4,657,027 A | 4/1987 | Paulsen | |

(Continued)

FOREIGN PATENT DOCUMENTS

JP      06317566 A      11/1994

(Continued)

OTHER PUBLICATIONS

Edwards Lifesciences (2000)."Safe and Accurate Blood Sampling in Surgery and Intensive Care", Edwards Lifesciences LLC (Vamp Plus System) located at: <http://www.edwards.com/NR/rdonlyres/8B42Fa81-225A-4204-BBE3-6ED73A376CC2/0/1141VAMPPlus04Update.pdf>, last visited on Jan. 16, 2008, four pages.

(Continued)

*Primary Examiner* — Patricia Mallari
(74) *Attorney, Agent, or Firm* — Morrison & Foerster LLP

(57) ABSTRACT

The present invention relates generally to systems, apparatuses, and methods for obtaining a fluid sample from a patient. In particular, the present invention relates to a various types of fluid access interfaces for enabling contact between a patient blood sample and blood parameter sensors for the measurement of physiological parameters and blood constituents.

13 Claims, 15 Drawing Sheets

U.S. PATENT DOCUMENTS

| | | |
|---|---|---|
| 4,696,309 A | 9/1987 | Stephan |
| 4,743,228 A | 5/1988 | Butterfield |
| 4,786,394 A | 11/1988 | Enzer et al. |
| 4,796,644 A | 1/1989 | Polaschegg |
| 4,838,855 A | 6/1989 | Lynn |
| 4,871,439 A | 10/1989 | Enzer et al. |
| 4,872,813 A | 10/1989 | Gorton et al. |
| 4,878,896 A | 11/1989 | Garrison et al. |
| 4,919,596 A | 4/1990 | Slate et al. |
| 4,928,694 A | 5/1990 | Maxwell |
| 4,934,369 A | 6/1990 | Maxwell |
| 4,951,669 A | 8/1990 | Maxwell et al. |
| 5,002,066 A | 3/1991 | Simpson et al. |
| 5,019,974 A | 5/1991 | Beckers |
| 5,035,704 A | 7/1991 | Lambert et al. |
| 5,037,396 A | 8/1991 | Streeter |
| 5,048,537 A | 9/1991 | Messinger |
| 5,077,010 A | 12/1991 | Ishizaka et al. |
| 5,096,669 A | 3/1992 | Lauks et al. |
| 5,134,079 A | 7/1992 | Cusack et al. |
| 5,135,489 A | 8/1992 | Jepson et al. |
| 5,148,811 A | 9/1992 | Messinger |
| 5,165,406 A | 11/1992 | Wong |
| 5,178,603 A | 1/1993 | Prince |
| 5,195,963 A | 3/1993 | Yafuso et al. |
| 5,216,597 A | 6/1993 | Beckers |
| 5,225,063 A | 7/1993 | Gumbrecht et al. |
| 5,237,993 A | 8/1993 | Skrabal |
| 5,252,213 A | 10/1993 | Ahmad et al. |
| 5,271,815 A | 12/1993 | Wong |
| 5,307,263 A | 4/1994 | Brown |
| 5,325,853 A | 7/1994 | Morris et al. |
| 5,325,867 A | 7/1994 | Skrabal et al. |
| 5,330,634 A | 7/1994 | Wong et al. |
| 5,335,658 A | 8/1994 | Bedingham |
| 5,345,932 A | 9/1994 | Yafuso et al. |
| 5,368,029 A | 11/1994 | Holcombe et al. |
| 5,368,555 A | 11/1994 | Sussman et al. |
| 5,379,764 A | 1/1995 | Barnes et al. |
| 5,380,665 A | 1/1995 | Cusack et al. |
| 5,421,328 A | 6/1995 | Bedingham |
| 5,431,174 A | 7/1995 | Knute |
| 5,462,052 A | 10/1995 | Gehrich et al. |
| 5,505,828 A | 4/1996 | Wong et al. |
| 5,531,672 A | 7/1996 | Lynn |
| 5,536,249 A | 7/1996 | Castellano et al. |
| 5,569,186 A | 10/1996 | Lord et al. |
| 5,582,184 A | 12/1996 | Erickson et al. |
| 5,638,828 A | 6/1997 | Lauks et al. |
| 5,665,065 A | 9/1997 | Colman et al. |
| 5,695,623 A | 12/1997 | Michel et al. |
| 5,697,366 A | 12/1997 | Kimball et al. |
| 5,697,899 A | 12/1997 | Hillman et al. |
| 5,720,924 A | 2/1998 | Eikmeier et al. |
| 5,741,211 A | 4/1998 | Renirie et al. |
| 5,746,217 A | 5/1998 | Erickson et al. |
| 5,747,666 A | 5/1998 | Willis |
| 5,758,643 A | 6/1998 | Wong et al. |
| 5,800,387 A | 9/1998 | Duffy et al. |
| 5,804,048 A | 9/1998 | Wong et al. |
| 5,820,570 A | 10/1998 | Erickson et al. |
| 5,871,494 A | 2/1999 | Simons et al. |
| 5,902,253 A | 5/1999 | Pfeiffer et al. |
| 5,928,880 A | 7/1999 | Wilding et al. |
| 5,932,175 A | 8/1999 | Knute et al. |
| 5,947,911 A | 9/1999 | Wong et al. |
| 5,971,941 A | 10/1999 | Simons et al. |
| 5,976,085 A | 11/1999 | Kimball et al. |
| 6,017,318 A | 1/2000 | Gauthier et al. |
| 6,027,479 A | 2/2000 | Alei et al. |
| 6,036,924 A | 3/2000 | Simons et al. |
| 6,066,243 A | 5/2000 | Anderson et al. |
| 6,071,294 A | 6/2000 | Simons et al. |
| 6,080,116 A | 6/2000 | Erickson et al. |
| 6,099,484 A | 8/2000 | Douglas et al. |
| 6,113,554 A | 9/2000 | Gilcher et al. |
| 6,117,290 A | 9/2000 | Say et al. |
| 6,123,827 A | 9/2000 | Wong et al. |
| 6,128,519 A | 10/2000 | Say |
| 6,175,752 B1 | 1/2001 | Say et al. |
| 6,184,029 B1 | 2/2001 | Wilding et al. |
| 6,188,648 B1 | 2/2001 | Olsen |
| 6,192,891 B1 | 2/2001 | Gravel et al. |
| 6,203,759 B1 | 3/2001 | Pelc et al. |
| 6,233,471 B1 | 5/2001 | Berner et al. |
| 6,251,660 B1 | 6/2001 | Muir et al. |
| 6,272,364 B1 | 8/2001 | Kurnik |
| 6,279,511 B1 | 8/2001 | Loughnane |
| 6,296,615 B1 | 10/2001 | Brockway et al. |
| 6,302,855 B1 | 10/2001 | Lav et al. |
| 6,372,182 B1 | 4/2002 | Mauro et al. |
| 6,375,627 B1 | 4/2002 | Mauze et al. |
| 6,464,849 B1 | 10/2002 | Say et al. |
| 6,472,220 B1 | 10/2002 | Simons et al. |
| 6,484,046 B1 | 11/2002 | Say et al. |
| 6,540,672 B1 | 4/2003 | Simonsen et al. |
| 6,540,890 B1 | 4/2003 | Bhullar et al. |
| 6,541,266 B2 | 4/2003 | Modzelewski et al. |
| 6,546,269 B1 | 4/2003 | Kurnik |
| 6,558,351 B1 | 5/2003 | Steil et al. |
| 6,561,989 B2 | 5/2003 | Whitson |
| 6,565,509 B1 | 5/2003 | Say et al. |
| 6,572,545 B2 | 6/2003 | Knobbe et al. |
| 6,576,101 B1 | 6/2003 | Heller et al. |
| 6,595,919 B2 | 7/2003 | Berner et al. |
| 6,602,205 B1 | 8/2003 | Erickson et al. |
| 6,602,702 B1 | 8/2003 | McDevitt et al. |
| 6,605,471 B1 | 8/2003 | Lundsgaard et al. |
| 6,612,111 B1 | 9/2003 | Hodges et al. |
| 6,645,359 B1 | 11/2003 | Bhullar et al. |
| 6,653,091 B1 | 11/2003 | Dunn et al. |
| 6,656,114 B1 | 12/2003 | Poulsen et al. |
| 6,656,428 B1 | 12/2003 | Clark et al. |
| 6,659,959 B2 | 12/2003 | Brockway et al. |
| 6,666,821 B2 | 12/2003 | Keimel |
| 6,669,663 B1 | 12/2003 | Thompson |
| 6,695,803 B1 | 2/2004 | Robinson et al. |
| 6,736,783 B2 | 5/2004 | Blake et al. |
| 6,740,072 B2 | 5/2004 | Starkweather et al. |
| 6,743,633 B1 | 6/2004 | Hunter |
| 6,749,567 B2 | 6/2004 | Davis et al. |
| 6,755,807 B2 | 6/2004 | Risk, Jr. et al. |
| 6,755,949 B1 | 6/2004 | Bhullar et al. |
| 6,764,462 B2 | 7/2004 | Risk, Jr. et al. |
| 6,768,879 B2 | 7/2004 | Kosuge |
| 6,780,297 B2 | 8/2004 | Matsumoto et al. |
| 6,800,074 B2 | 10/2004 | Henley et al. |
| 6,814,843 B1 | 11/2004 | Bhullar et al. |
| 6,814,844 B2 | 11/2004 | Bhullar et al. |
| 6,824,533 B2 | 11/2004 | Risk, Jr. et al. |
| 6,849,237 B2 | 2/2005 | Housefield et al. |
| 6,866,758 B2 | 3/2005 | Bhullar et al. |
| 6,872,297 B2 | 3/2005 | Mansouri et al. |
| 6,872,358 B2 | 3/2005 | Hagen et al. |
| 6,875,619 B2 | 4/2005 | Blackburn |
| 6,902,703 B2 | 6/2005 | Marquiss et al. |
| 6,911,182 B2 | 6/2005 | Tegeler et al. |
| 6,911,621 B2 | 6/2005 | Bhullar et al. |
| 6,923,764 B2 | 8/2005 | Aceti et al. |
| 6,988,996 B2 | 1/2006 | Roe et al. |
| 7,004,928 B2 | 2/2006 | Aceti et al. |
| 7,022,219 B2 | 4/2006 | Mansouri et al. |
| 7,152,616 B2 | 12/2006 | Zucchelli et al. |
| 7,157,049 B2 | 1/2007 | Valencia et al. |
| 7,162,290 B1 | 1/2007 | Levin |
| 7,179,423 B2 | 2/2007 | Böhm et al. |
| 7,198,606 B2 | 4/2007 | Boecker et al. |
| 7,232,547 B2 | 6/2007 | Rusch et al. |
| 7,244,232 B2 | 7/2007 | Connelly et al. |
| 7,244,393 B2 | 7/2007 | Kaylor et al. |
| 7,258,672 B2 | 8/2007 | Hansson et al. |
| 7,303,727 B1 | 12/2007 | Dubrow et al. |
| 7,338,802 B2 | 3/2008 | Frischauf et al. |
| 7,378,270 B2 | 5/2008 | Azarnia et al. |
| 2003/0191415 A1 | 10/2003 | Moerman et al. |
| 2004/0138688 A1 | 7/2004 | Giraud |
| 2006/0079809 A1* | 4/2006 | Goldberger et al. .......... 600/576 |

| 2006/0188407 | A1 | 8/2006 | Gable et al. |
| 2006/0235348 | A1 | 10/2006 | Callicoat et al. |
| 2006/0278537 | A1 | 12/2006 | Cai et al. |
| 2006/0281187 | A1 | 12/2006 | Emery et al. |

FOREIGN PATENT DOCUMENTS

| WO | WO-91/16416 | A1 | 10/1991 |
| WO | WO-02/080762 | A1 | 10/2002 |
| WO | WO-02/100254 | A2 | 12/2002 |
| WO | WO-02/100254 | A3 | 12/2002 |
| WO | WO-03/080166 | A1 | 10/2003 |
| WO | WO-2004/047642 | A1 | 6/2004 |
| WO | WO-2004/052204 | A1 | 6/2004 |
| WO | WO-2004/056269 | A1 | 7/2004 |
| WO | WO-2007/137285 | A2 | 11/2007 |
| WO | WO-2007/137285 | A3 | 11/2007 |

OTHER PUBLICATIONS

Edwards Lifesciences (2002) "Edward Vamp and Vamp Jr. Systems," located at: <http://www.edwards.com/Products/PressureMonitoring/VAMPSystemBrochurePDF.htm>, last visited on Jan. 16, 2008, four pages.

Genexel-Sien, Inc. (2006) "Introducing DUO-CARE Combined Blood Glucose and Wrist Blood Pressure Monitor," located at: www.duo-care.com/01product.html <http://www.duo-care.com/01product.html>, last visited on Jan. 2, 2008, one page.

International Preliminary Report on Patentability mailed on Dec. 16, 2008, for PCT Application No. PCT/US2006/045642, filed on Nov. 28, 2006, seven pages.

International Preliminary Report on Patentability mailed on Nov. 28, 2008, for PCT Application No. PCT/US/2007/069546, filed on May 23, 2007, five pages.

International Preliminary Report on Patentability mailed on Nov. 28, 2008, for PCT Application No. PCT/US2007/069542, filed on May 23, 2007, five pages.

International Preliminary Report on Patentability mailed on Jun. 12, 2008 for PCT Application No. PCT/US06/045359, filed on Nov. 27, 2006, six pages.

International Search Report mailed on Jun. 10, 2008, for PCT Application No. PCT/US07/69542, filed on May 23, 2007, one page.

International Search Report mailed on May 23, 2007, for PCT Application No. PCT/US06/24167, filed on Jun. 20, 2006, one page.

International Search Report mailed on Aug. 27, 2007, for PCT Application No. PCT/US06/45359, filed on Nov. 27, 2006, one page.

International Search Report mailed Sep. 27, 2007, for PCT Application No. PCT/US06/45440, one page.

Lifescan, Inc. (Dates from 1996-2006). "OneTouch Lancing Devices," located at: <http://lifescan.com/products/lancing>, last visited on Jan. 2, 2008, three pages.

Lifescan, Inc. (Dates from 1996-2006). "OneTouch SureStep Test Strips for use with OneTouch Surestep Meters", located at: <http://www.lifescan.com/products/teststrips/surestep>, last visited on Jan. 2, 2008, two pages.

Lifescan, Inc. (2001). "Lifescan Makes Getting Accurate Glucose Results Perfectly Easy," located at: <http://www.lifescan.net/pdf/hospital/ss_technology.pdf>, last visited on Jan. 16, 2008, five pages.

Lifescan, Inc. (2002). "OneTouch SureStep Blood Glucose Monitoring System Owner's Manual," located at: <http://www.lifescan.com/pdf/ss_ob.pdf>, last visited on Jan. 2, 2008, eighty-four pages.

ROCHE (2008) "Accu-Chek Compact Plus DiabetesTest Strips," located at: <http://www.accu-chek.com/us/rewrite/generalContent/en_US/article/ACCM_general_article_2656.htm>, last visited on Jan. 14, 2008, two pages.

Via Medicial Corporation (Dates from 1988-1998). "Study on On-Line Hematocrit and Glucose Analysis Animal Study," Infusion Pump FDA documents submitted by Via Medical Corporation, one hundred and eighty-four pages.

* cited by examiner

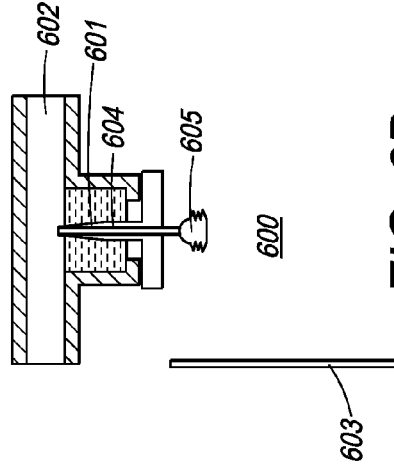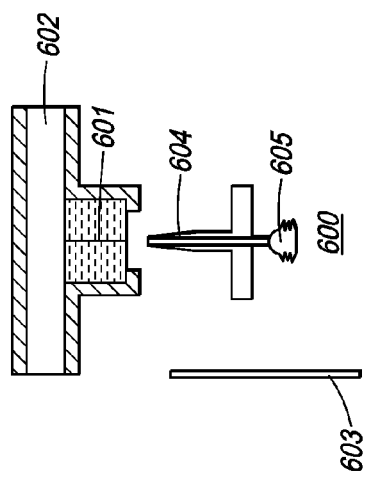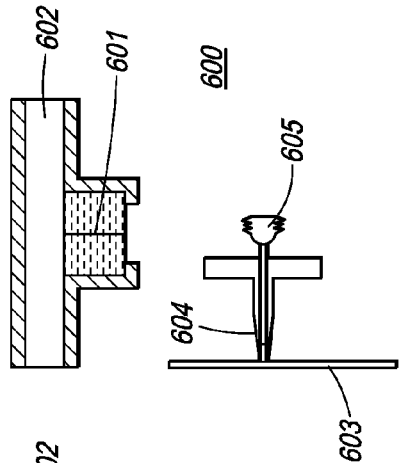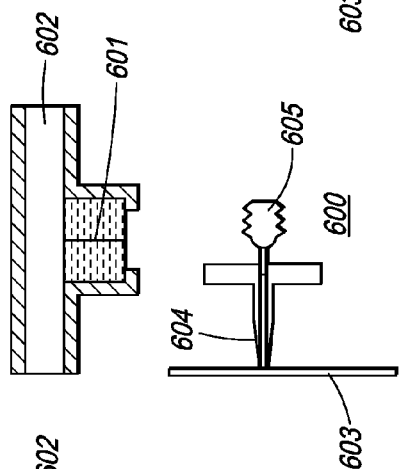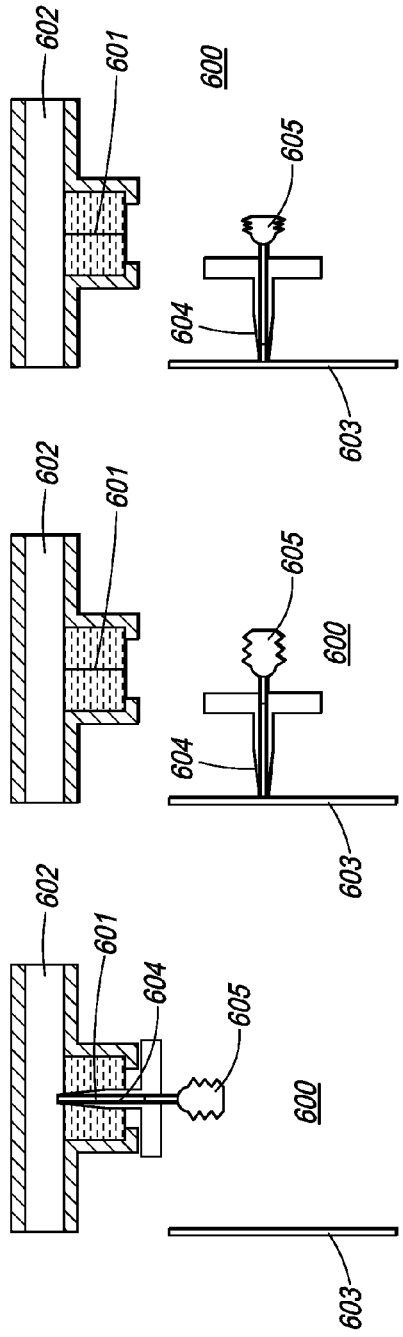

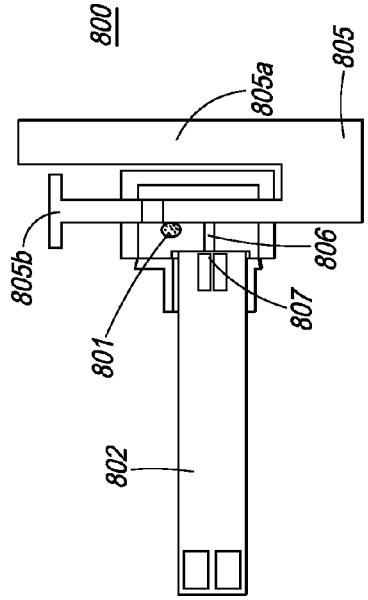
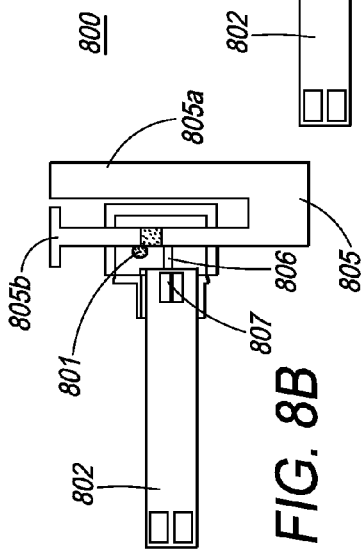
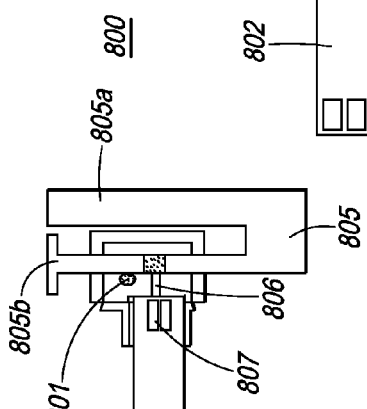
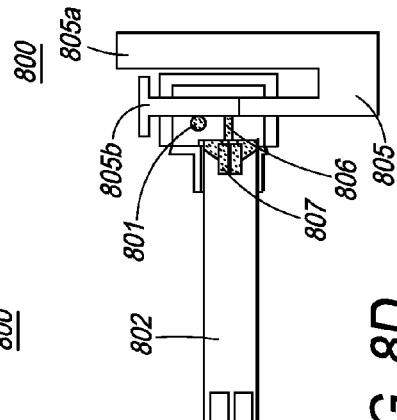
FIG. 8A
FIG. 8B
FIG. 8C
FIG. 8D

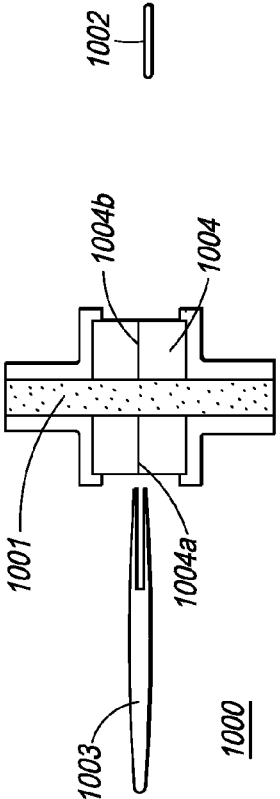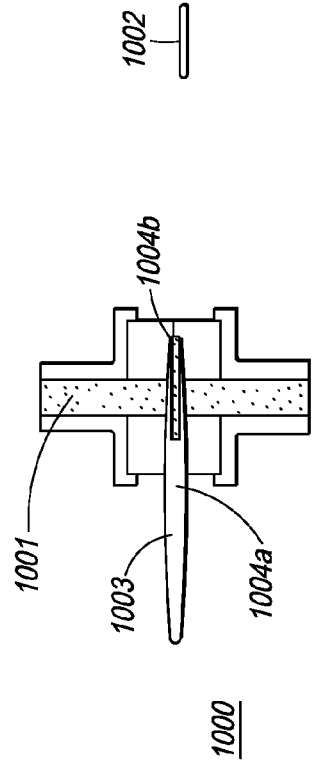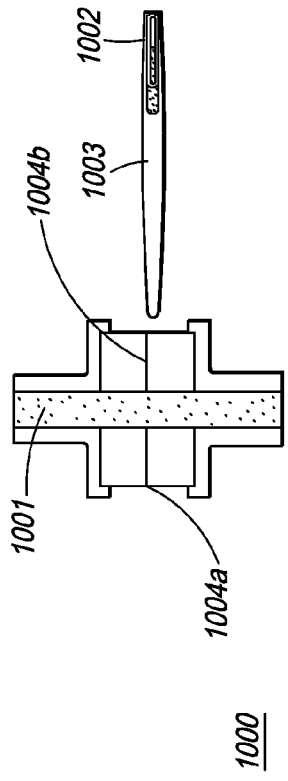
FIG. 10A
FIG. 10B
FIG. 10C

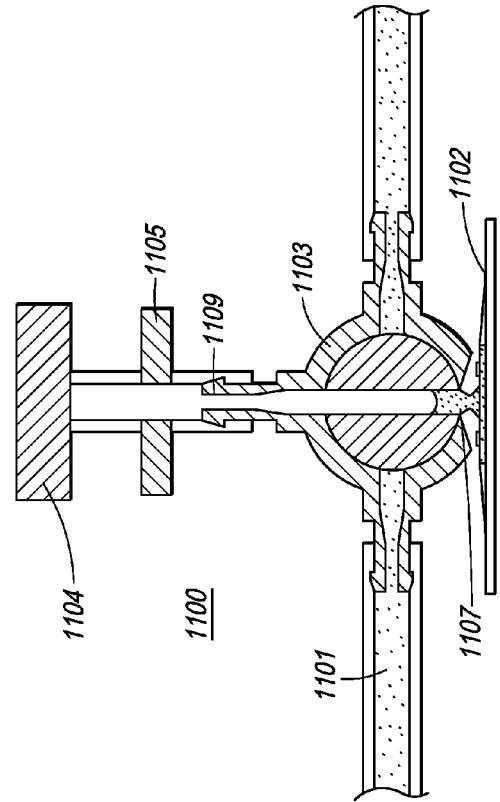
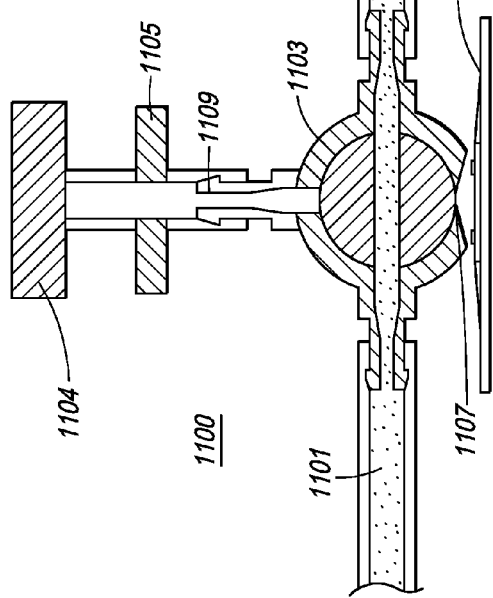

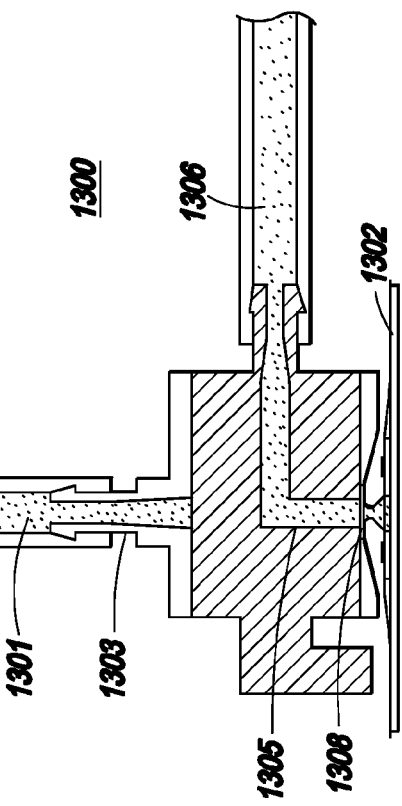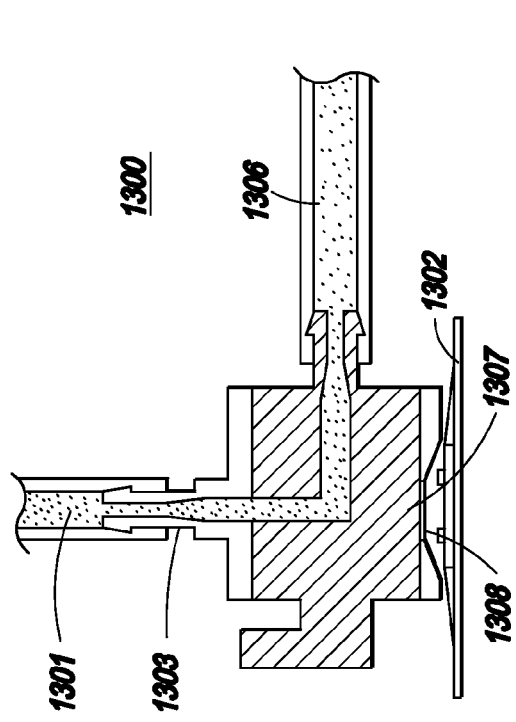

FLUID ACCESS INTERFACE

FIELD OF THE INVENTION

The present invention relates generally to systems, apparatuses, and methods for obtaining a fluid sample from a patient. In particular, the present invention relates to a fluid access interface for accessing a blood sample present in tubing, such as, for example, a vascular access line connected to a patient. In addition, the present invention relates to a fluid access interface for enabling contact between a patient blood sample and sensors, such as blood parameter testing strips, for the measurement of physiological parameters and blood constituents. More specifically, the fluid access interfaces of the present invention may be used in conjunction with a system for automated blood glucose measurement and testing.

BACKGROUND OF THE INVENTION

Patient blood chemistry and monitoring of patient blood chemistry are important diagnostic tools in patient care. For example, the measurement of blood analytes and parameters often give much needed patient information in the proper amounts and time periods over which to administer a drug. Blood analytes and parameters tend to change frequently, however, especially in the case of a patient under continual treatment, thus making the measurement process tedious, frequent, and difficult to manage.

Blood glucose levels must be maintained within a narrow range (about 3.5-6.5 mM). Glucose levels lower than this range (hypoglycemia) may lead to mental confusion, coma, or death. High glucose levels (hyperglycemia) have been linked to severe complications, including kidney damage, neural damage, and blindness.

Conventional glucose measurement techniques require lancing a convenient part of the body (normally a fingertip) with a lancet, milking the finger to produce a drop of blood, and depositing the drop of blood on a measurement device (such as an glucose testing strip). This lancing method is both painful and inconvenient for the patient. The pain and inconvenience has additional and more serious implications of noncompliance. Patients generally avoid maintaining the recommended regimen of blood glucose measurement and thereby run the risk of improper glucose levels and consequent harmful effects.

The conventional Point-of-Care (POC) techniques for diagnostic blood testing are routinely performed manually at the bedside using a small sample of blood.

SureStep® Technology, developed by Lifescan, is one example of a conventional Point-of-Care diagnostic system. The SureStep® Technology, in its basic form allows for simple, single button testing, quick results, blood sample confirmation, and test memory. In operation, the SureStep® Point-of-Care system employs three critical steps for performance. In a first step, the blood sample is applied to the test strip. The blood sample is deposited on an absorbent pad, which is touchable and promotes quick, convenient, and safe sample application. In addition, blood is retained and not transferred to other surfaces. The sample then flows one way through the porous pad to the reagent membrane, where the reaction occurs. The reagent membrane is employed to filter out red blood cells while allowing plasma to move through. In a second step, the glucose reacts with the reagents in the test strip. Glucose in the sample is oxidized by glucose oxidase (GO) in the presence of atmospheric oxygen, forming hydrogen peroxide ($H_2O_2$). $H_2O_2$ reacts with indicator dyes using horseradish peroxidase (HRP), forming a chromophore or light-absorbing dye. The intensity of color formed at the end of the reaction is proportional to the glucose present in the sample.

In a third step, the blood glucose concentration is measured with SureStep® meters. Reflectance photometry quantifies the intensity of the colored product generated by the enzymatic reaction. The colored product absorbs the light—the more glucose in a sample (and thus the more colored product on a test strip), the less reflected light. A detector captures the reflected light, converts it into an electronic signal, and translates it into a corresponding glucose concentration. The system is calibrated to give plasma glucose values.

Prior art devices have conventionally focused upon manually obtaining blood samples from in-dwelling catheters. Such catheters may be placed in venous or arterial vessels, centrally or peripherally. For example, Edwards LifeSciences' VAMP Plus Closed Blood Sampling System provides a safe method for the withdrawal of blood samples from pressure monitoring lines. The blood sampling system is designed for use with disposable and reusable pressure transducers and for connection to central line catheters, venous, and arterial catheters where the system can be flushed clear after sampling. The blood sampling system mentioned above, however, is for use only on patients requiring periodic manual withdrawal of blood samples from arterial and central line catheters that are attached to pressure monitoring lines.

The VAMP Plus design provides a needleless blood sampling system, employing a blunt cannula for drawing of blood samples. In addition, a self-sealing port reduces the risk of infection. The VAMP Plus system employs a large reservoir with two sample sites. Two methods may be used to draw a blood sample in the VAMP Plus Blood Sampling System. The first method, the syringe method for drawing blood samples, first requires that the VAMP Plus is prepared for drawing a blood sample by drawing a clearing volume (preferred methods provided in the literature). To draw a blood sample, it is recommended that a preassembled packaged VAMP NeedleLess cannula and syringe is used. Then, the syringe plunger should be depressed to the bottom of the syringe barrel. The cannula is then pushed into the sampling site. The blood sample is then drawn into the syringe. A Blood Transfer Unit is then employed to transfer the blood sample from the syringe to the vacuum tubes.

The second method allows for a direct draw of blood samples. Again, the VAMP Plus is first prepared for drawing a blood sample by drawing a clearing volume. To draw a blood sample, the VAMP Direct Draw Unit is employed. The cannula of the Direct Draw Unit is pushed into the sampling site. The selected vacuum tube is inserted into the open end of the Direct Draw Unit and the vacuum tube is filled to the desired volume.

The abovementioned prior art systems, however, have numerous disadvantages. In particular, manually obtaining blood samples from in-dwelling catheters tends to be cumbersome for the patient and healthcare providers.

In the light of above described disadvantages, there is a need for improved methods and systems that can provide comprehensive blood parameter testing.

What is also needed is a programmable, automated system and method for obtaining blood samples for testing certain blood parameters and data management of measurement results, thus avoiding human recording errors and providing for central data analysis and monitoring.

In addition, what is needed are systems, methods, and apparatuses for enabling fluid sampling in automated blood parameter testing systems.

More specifically, what is needed are fluid sampling interface apparatuses and methods for using such apparatuses with automated blood parameter testing systems.

SUMMARY OF THE INVENTION

The present invention is directed toward a plurality of embodiments capable of accessing a blood sample, present in a vascular access line connected to a patient, or any other form of tubing. In one embodiment, the present invention is a device for accessing a blood sample from a patient and measuring blood constituents, comprising a single use flexible transfer tube having a shape, wherein the single use transfer tube is used to provide a direct fluid flow path to a test substrate and wherein an alteration in the shape of the tube causes the tube to move from an open state to a closed state. In an open state, the tube provides a blood sample to a proximally located testing site, such as a testing strip or sensor.

In another embodiment, the present invention is a device for accessing a blood sample from a patient and bringing the blood samples to a transfer tube in combination with a test strip holder. The test strip holder positions a test strip for fluid dispensing and mechanical handling. The distal end may be an end-access capillary test strip for glucose measurement.

The transfer tube may be used to access fluid from a main fluid line to determine the concentration of at least one analyte, wherein the main fluid tube further comprises a tube originating from a vascular access point, a pump fixedly attached to the tube, a valve fixedly attached to the tube and located above the pump mechanism, at least one measurement element, a needle-less port, for accessing the main fluid tube; and an electronic meter.

In another embodiment, the present invention is directed toward a device for accessing a blood sample, present in a vascular access line connected to a patient or any other form of tubing and measuring blood constituents, comprising a transfer tube with a closed end used to remove fluid from a needle-less access port and to a test substrate, wherein the closed end of the transfer tube is a bulb which can be expanded and contracted to access a fluid sample.

Optionally, the transfer tube comprises a micro-syringe, wherein the micro-syringe comprises a plunger to remove and deposit a fluid sample onto a test substrate. The closed-end transfer tube is used to access fluid from a main fluid line to determine the concentration of at least one analyte, wherein the main fluid line further comprises a tube originating from a vascular access point, a pump fixedly attached to the tube, a valve fixedly attached to the tube and located above the pump mechanism, at least one measurement element, a needle-less port for accessing the main fluid line, and an electronic meter.

In another embodiment, the present invention is directed toward a device for accessing a blood sample, present in a vascular access line connected to a patient or any other form of tubing and measuring blood constituents, comprising a piston pump, wherein the piston pump is connected to a transfer tube and said piston pump is used to remove a fluid sample and deliver the fluid sample to a test substrate. The piston pump is used to access fluid from a main fluid line to determine the concentration of at least one analyte, wherein the fluid line is further used with a tube originating from a vascular access point, a pump fixedly attached to the tube, a valve fixedly attached to the tube and located above the pump mechanism, at least one measurement element, a needle-less port, for accessing the main fluid line, and an electronic meter.

In another embodiment, the present invention is directed toward a device for accessing a blood sample, present in a vascular access line connected to a patient or any other form of tubing and measuring blood constituents, comprising a shuttle, wherein said shuttle is a single-use device used to facilitate drawing a sanitary and uncontaminated fluid sample through a sampling port without passing back through the sampling port.

Optionally, the shuttle device penetrates through a dual-sided needle-less port. The shuttle device is used to access fluid from a main fluid line to determine the concentration of at least one analyte, wherein the fluid line is further used with a tube originating from a vascular access point, a pump fixedly attached to the tube, a valve fixedly attached to the tube and located above the pump mechanism, at least one measurement element, a dual-sided needle-less port, for accessing the main fluid line, and an electronic meter.

In another embodiment, the present invention is directed toward a device for accessing a blood sample, present in a vascular access line connected to a patient or any other form of tubing and measuring blood constituents, comprising an air jet fluid access port, which further comprises a valve and a low volume air pump. The air jet fluid access port is used to access fluid from a fluid line to determine the concentration of at least one analyte, wherein the fluid line is used with a tube originating from a vascular access point, a pump fixedly attached to the tube, a valve fixedly attached to the tube and located above the pump mechanism, at least one measurement element, a needle-less port, for facilitating access to the main fluid line, and an electronic meter.

In another embodiment, the present invention is directed toward a device for accessing a blood sample, present in a vascular access line connected to a patient or any other form of tubing and measuring blood constituents, comprising a distribution valve wherein said distribution valve is used to redirect a main flow of fluid to a side path. Optionally, the distribution valve is a by-pass valve. Optionally, the distribution valve has zero dead volume. Optionally, the distribution valve has a micro filter positioned at one or more ports. The micro-filter isolates the fluid inside the valve from contamination. The micro-filter is cleaned by purging fluid before and after sample collection. The distribution valve may include a sterile filter. The distribution valve may include a dispensing pump. The distribution valve is used to access fluid from a fluid line to determine the concentration of at least one analyte, wherein said line is used with a tube originating from a vascular access point, a pump fixedly attached to the tube, a valve fixedly attached to the tube and located above the pump mechanism, at least one measurement element, and an electronic meter.

In another embodiment, the disclosed inventions are used with an automated blood glucose analysis device further comprising an access device for gaining access to blood with a catheter; a pump to withdraw blood from the patient in a predetermined schedule; at least one sensor placed in contact with said blood by an action of the fluid access interfaces of the present invention; and a signal processor to measure a signal produced by the at least one sensor upon contact with said blood where the signal is indicative of said at least one predetermined parameter.

BRIEF DESCRIPTION OF THE DRAWINGS

These and other features and advantages of the present invention will be appreciated, as they become better understood by reference to the following Detailed Description when considered in connection with the accompanying drawings, wherein:

FIGS. 6A, 6B, 6C, 6D, and 6E depict the structure and operational steps of one embodiment of the fluid access interface of the present invention implemented as a transfer tube with one closed end;

FIGS. 8A, 8B, 8C, and 8D depict the structure and operational steps of one embodiment of the fluid access interface device of the present invention wherein a pump is employed;

FIGS. 10A, 10B, and 10C depict the structure and operational steps of one embodiment of the fluid access interface of the present invention wherein a shuttle and dual needle-less port are employed;

FIGS. 11A and 11B depict the structure and operational steps of one embodiment of the fluid access interface of the present invention implemented as an air jet fluid access port;

FIGS. 13A and 13B depict the structure and operational steps of another embodiment of the fluid access interface of the present invention, implemented as a distribution valve equipped with a filter;

DETAILED DESCRIPTION OF THE INVENTION

The present invention is directed towards an integrated, automated system for measurement and analysis of blood analytes and blood parameters. The present invention is also directed towards an automated blood parameter testing apparatus portion of the automated blood parameter analysis and measurement system. More specifically, the present invention is directed towards methods, apparatuses, and systems for accessing a blood sample, present in a vascular access line connected to a patient or any other form of tubing via a fluid access interface. In one embodiment, the fluid access interface methods, apparatuses, and systems are used for automated blood glucose testing.

In automatic operation, when fluid sampling is initiated, either by a pre-determined, programmed schedule or via operator input, the fluid access interface is activated and a fluid sample is drawn from the vascular access line connected to a patient or any other form of tubing. The system operates automatically to draw the fluid samples via a fluid access interface at suitable, programmable frequencies to analyze the drawn blood samples and obtain the desired blood readings such as glucose levels, hematocrit levels, hemoglobin blood oxygen saturation, blood gasses, lactates or any other parameter as would be evident to persons of ordinary skill in the art.

As referred to herein, the terms "blood analyte(s)" and "blood parameter(s)" refers to such measurements as, but not limited to, glucose level; ketone level; hemoglobin level; hematocrit level; lactate level; electrolyte level ($Na^+$, $K^+$, $Cl^-$, $Mg^{2+}$, $Ca^{2+}$); blood gases ($pO_2$, $pCO_2$, pH); cholesterol; bilirubin level; and various other parameters that can be measured from blood or plasma samples. The term "vascular access point(s)" refer to venous or arterial access points in the peripheral or central vascular system.

Reference will now be made in detail to specific embodiments of the invention. While the invention will be described in conjunction with specific embodiments, it is not intended to limit the invention to one embodiment. Thus, the present invention is not intended to be limited to the embodiments described, but is to be accorded the broadest scope consistent with the disclosure set forth herein.

In one embodiment, the present invention is a device for accessing a blood sample from a patient and measuring blood constituents, wherein the fluid access interface comprises a flexible transfer tube having a shape, wherein the transfer tube is used to provide a direct fluid flow path to a test substrate and wherein an alteration in the shape of the tube causes the tube to move from an open state to a closed state. In an open state, the test tube substrate provides a blood sample to a proximally located testing site, such as a testing strip or sensor.

Figure 1B:
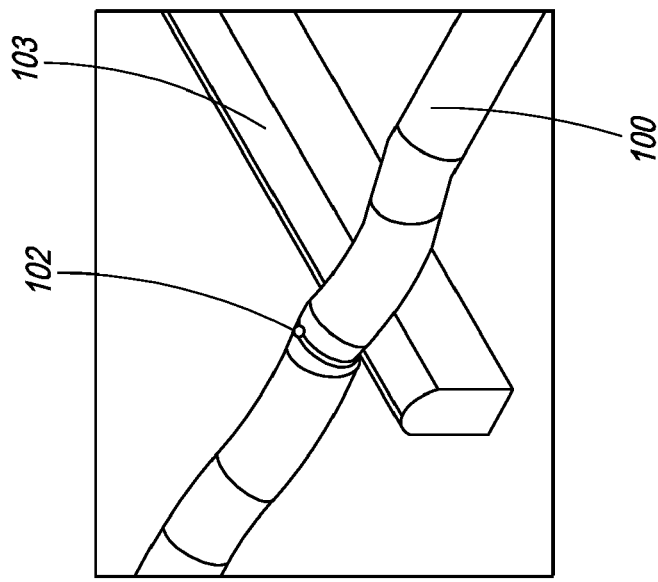
FIGS. 1A and 1B are illustrations of one embodiment of the fluid access interface device of the present invention, implemented as a flexible tube.
Figure 1A:
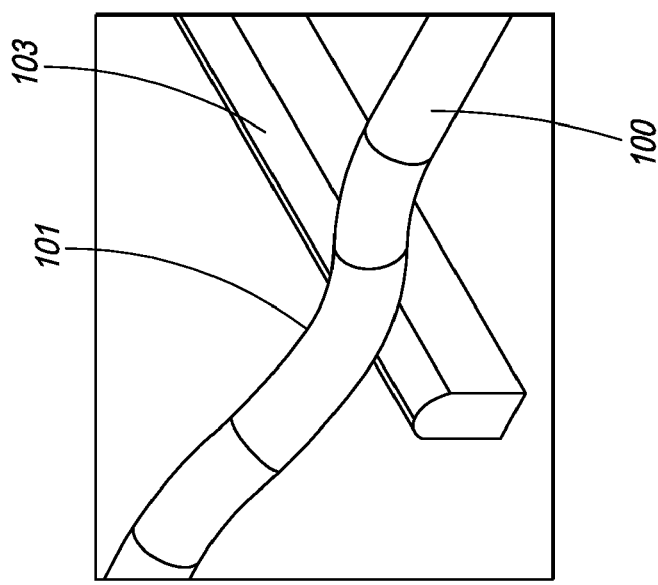

FIGS. 1a and 1b are illustrations of one embodiment of the fluid access interface of the present invention, wherein the flexible tube is employed. In a first embodiment, a fluid access interface is implemented as a flexible tube. Specifically, FIG. 1a is a depiction of flexible tube 100 wherein outlet 101 is in a closed state. FIG. 1b is a depiction of a bent flexible tube 100 wherein outlet 102 is in an open state. An alteration in the shape of the tube facilitates control of the outlet. The alteration of the tube shape can be facilitated by a member 103, which can be any structure, including a rod, stick, lever, or any linear extension. When flexible tube 100 is bent, as shown in FIG. 1b, the tube is split open, creating an open state and thus forming an outlet for a fluid sample. In an open state, outlet 102 may comprise a slit or hole, however, the opening is not limited to such configurations.

Figure 2:
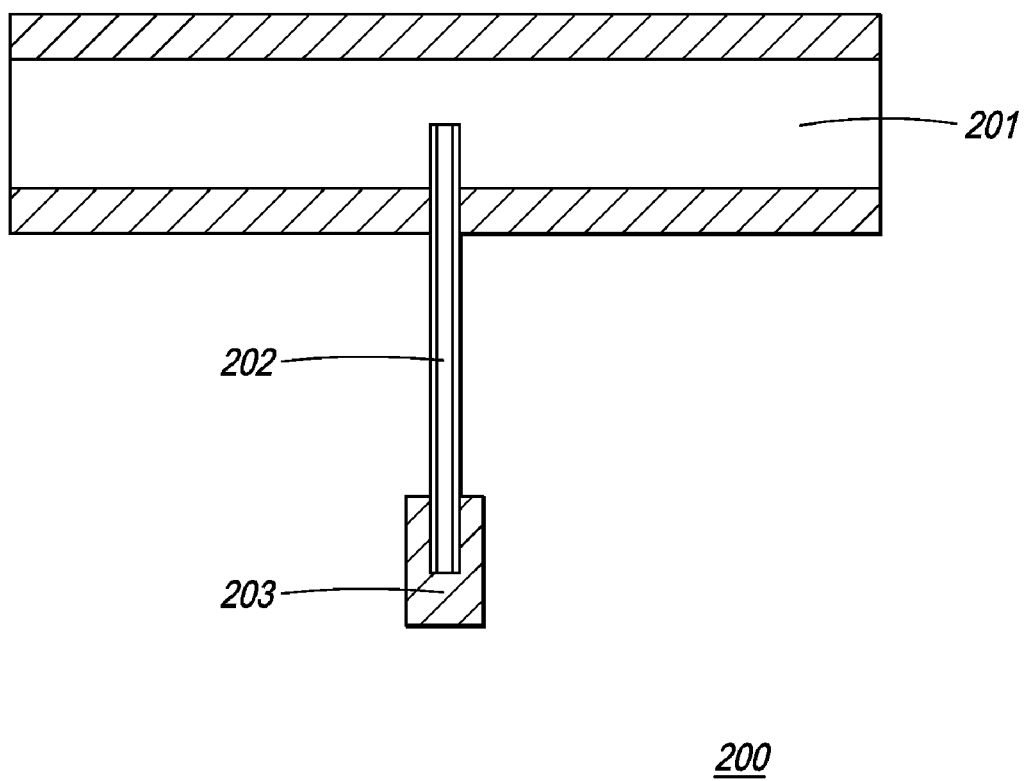
FIG. 2 depicts another embodiment of the fluid access interface device of the present invention.

FIG. 2 depicts another embodiment of a fluid access interface 200 wherein a transfer tube is employed. A fluid access interface is implemented as a transfer tube equipped with a cap or valve, used to extract fluid from a vascular access line connected to a patient or any other form of tubing. As shown in FIG. 2, the main fluid line 201 further comprises transfer tube 202, and end valve 203. In one embodiment, main fluid line 201 is a vascular access line connected to a patient. Preferably, transfer tube 202 is smaller in diameter than main fluid line 201. End valve 203 is used to draw fluid into transfer tube 202 for subsequent collection. When the transfer tube 202 is not in use, end valve 203 may serve as a cap, thus providing a sealed, sterile barrier.

Figure 3A:
FIGS. 3A, 3B, and 3C illustrate the structure and operational steps of one embodiment of the fluid access interface device of the present invention.
Figure 3C:
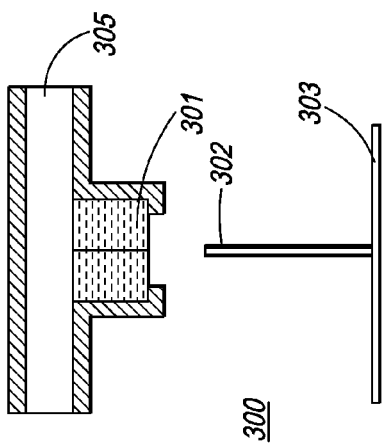
Figure 3B:

FIGS. 3a, 3b, and 3c illustrate the structure and operational steps of another embodiment of the fluid access interface of the present invention wherein a transfer tube is employed. As shown in FIG. 3a, the fluid access interface device 300 of the present invention is implemented as a transfer tube that is used to remove fluid from a main fluid line 305 connected to a patient. Main fluid line 305 further comprises seal 301. In one embodiment, seal 301 is a needle-less access port. The transfer tube 302 is positioned to come into contact with seal 301, extract a fluid sample (not shown) from main line 305, and subsequently deliver the fluid sample to a test substrate 303.

FIG. 3b illustrates fluid access interface device 300 in operation. The transfer tube 302 penetrates seal 301, accessing main fluid line 305. The transfer tube 302 is thus used to provide a direct flow path to the test substrate 303. As shown in FIG. 3c, after single use transfer tube 302 comes into contact with main fluid line 305, and more specifically, seal 301, transfer tube 302, now containing fluid, is extracted from seal 301. Single use transfer tube 302 subsequently transports fluid to the test substrate 303. After removal from the test unit, transfer tube 303 is disposed into an appropriate container.

Figure 4:
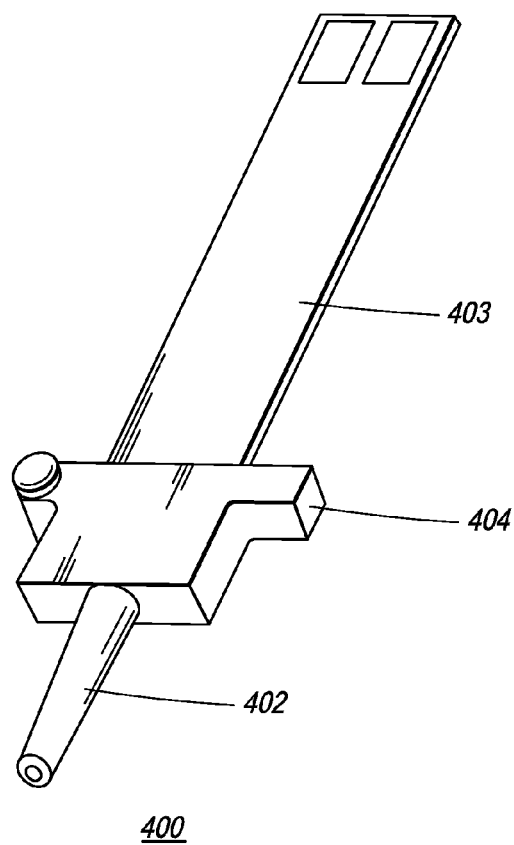
FIG. 4 illustrates another embodiment of the fluid access interface device of the present invention implemented as a transfer tube with an integrated test strip holder.

FIG. 4 illustrates another embodiment of a fluid access interface device 400 wherein a transfer tube 402 is integrated with a test strip holder 404. The integrated transfer tube 402 and test strip holder 404 is employed to access a fluid sample present in a vascular access line [not shown] connected to a patient or any other form of tubing. As previously shown, the main fluid line or vascular access line is preferably accessed via a needle-less port or seal. The integrated transfer tube 402 and test strip holder 404 is employed to position the test substrate 403 for proper fluid dispensing and mechanical handling. In one embodiment, the device 400 minimizes the amount of fluid required in a sample by reducing the dead volume of the structure and is optimally designed so that fluid flow is not impeded. Device 400 is also optimally shaped to effectuate capillary flow. Excess fluid resides in the area around the test substrate and single use transfer tube. The operation of the transfer tube has already been described with respect to FIG. 3 and will not be repeated herein. In operation of device 400, the fluid is delivered to the test substrate 403 via the transfer tube 402.

Figure 5:
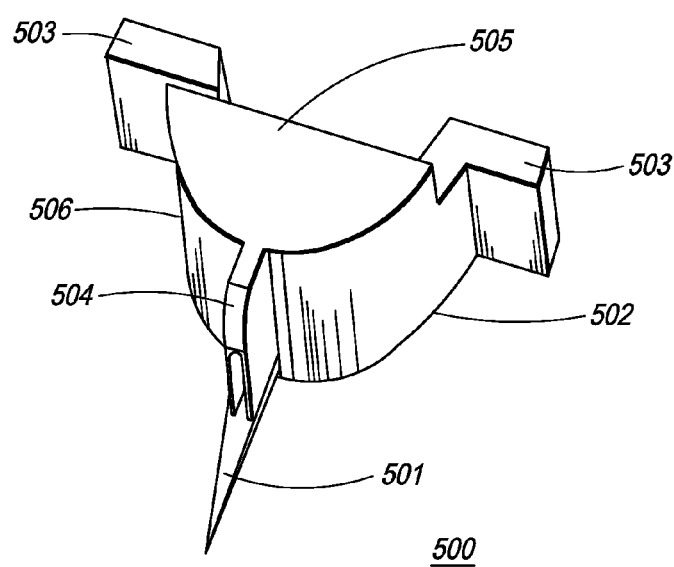
FIG. 5 illustrates a lancet structure.

FIG. 5 illustrates a portion of one embodiment of a fluid access interface designed to access a blood sample through the skin of a person. Lancet 500 is used to access a blood sample by using sharp protusion 501 to enter through a patient's skin. Sharp protusion 501 is physically integrated with edge 504 that is attached to structure 502. Structure 502 comprises a curved base 506 and two faces 505 curved to conform to the shape of the curved base 506 and having a linear top side. Integrally formed with the structure 502 are handles 503 which are flattened protusions designed to allow a person or mechanical actuator to hold and push the sharp protusion 501 into a patient's skin.

FIGS. 6a, 6b, 6c, 6d, and 6e illustrate the operational steps of one embodiment of the fluid access interface device of the present invention implemented as a transfer tube with a closed end forming a bulb. As shown in FIG. 6a, device 600 is a fluid access interface for accessing a blood sample, present in a main fluid line connected to a patient or any other form of tubing. In one embodiment, the fluid access interface 600 accesses the fluid sample from a needle-less access port or seal 601 attached to main fluid line 602. The fluid sample is subsequently delivered to test substrate 603. In one embodiment, fluid access interface device 600 comprises a transfer tube 604 with closed end 605, which is flexible and can be expanded and contracted to access a fluid sample and subsequently deposit the sample on a test substrate.

As shown in FIG. 6b, in operation, transfer tube 604 of device 600 is used to penetrate the needle-less access port or seal 601 of main fluid line 602. Now referring to FIG. 6c, closed end 605 of device 600 is expanded, thus withdrawing a fluid sample. As shown in FIG. 6d, the device is removed from the needle-less access port 601 and positioned on the test substrate 603. Finally, as shown in FIG. 6e, the closed end 605 of the device 600 is contracted depositing the fluid on the test substrate.

Figure 7:
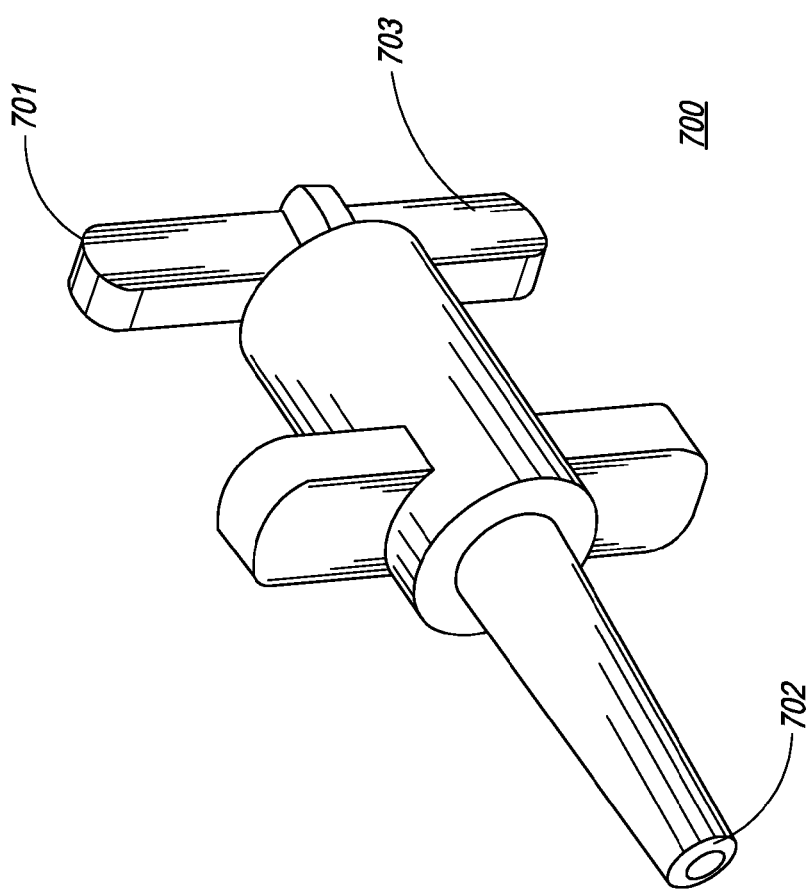
FIG. 7 depicts another embodiment of the fluid access interface of the present invention implemented as a transfer tube equipped with a micro-syringe on one end.

FIG. 7 depicts one embodiment of the fluid access interface of the present invention implemented as a transfer tube equipped with a micro-syringe on one end. The fluid access interface is employed to access a fluid sample, present in a main fluid line connected to a patient or any other form of tubing. In one embodiment, the fluid access interface 700 accesses the fluid sample from a needle-less access port (not shown) attached to the main fluid line (not shown) and delivers the fluid sample to a test substrate using a plunger-type device that regulates fluid volume. Device 700 comprises two ends—a distal end 701 and a proximate end 702. Proximate end 702 is preferably sized and shaped to penetrate a needle-less access port (not shown). Distal end 701 further comprises plunger 703, which is pulled and pushed to remove and deposit the fluid sample on the test substrate. Fluid access interface device 700 is similar in operation to the device described above with respect to FIG. 6 and thus, operational characteristics will not be repeated herein.

FIGS. 8a, 8b, 8c, and 8d illustrate the structure and operational steps of one embodiment of the fluid access interface of the present invention. The fluid access interface, implemented as a piston pump, is employed to access a fluid sample, present in a main fluid line connected to a patient or any other form of tubing. In one embodiment, the fluid access interface 800 accesses the fluid sample from a needle-less access port or seal attached to the main fluid line and delivers the fluid sample to a test substrate.

Referring now to FIG. 8a, a fluid sample is transferred from main fluid line 801 to a test substrate 802, via fluid access interface 800. In one embodiment, fluid access interface 800 comprises piston 805. Piston 805 further comprises piston chamber 805a and piston pump 805b. Piston 805 is employed to draw a bolus of fluid (not shown) from the main fluid line 801 into a cylinder 806, as shown in FIG. 8b. As shown in FIG. 8c, the bolus of fluid is then transported to the opening of test port 807 through cylinder 806. The bolus of fluid is then pushed to test substrate 802, as shown in FIG. 8d. Fluid access interface 800 may be implemented in several configurations, including, but not limited to multiple-use or single-use and/or with a multiple device configuration, such as a stack.

Figure 9:
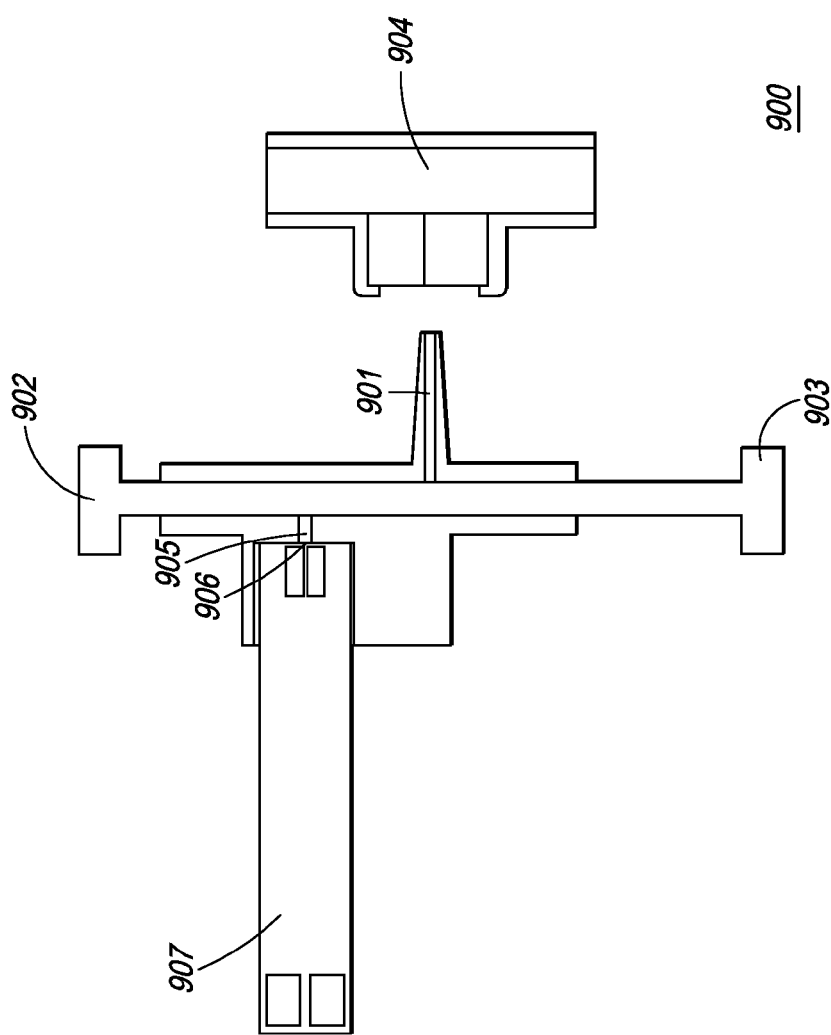
FIG. 9 is a cross-sectional view of one embodiment of the fluid access interface of the present invention implemented as a transfer tube equipped with a pump.

FIG. 9 is a cross-sectional view of one embodiment of the fluid access interface device of the present invention wherein a transfer tube further comprising a piston pump is employed to access a fluid sample, present in a main fluid line connected to a patient or any other form of tubing. In one embodiment, the fluid access interface 900 accesses the fluid sample from a needle-less access port or seal attached to the main fluid line and delivers the fluid sample to a test substrate.

Fluid access interface device 900 comprises a transfer tube 901 and pistons 902 and 903. Pistons 902 and 903 draw a bolus of fluid from main fluid line 904 via transfer tube 901 into a cylinder 905. The drawn bolus of fluid is then transported alongside cylinder 905 to the test access port entrance 906 and subsequently pushes the fluid through to test substrate 907. Device 900 can be employed in many configurations, including, but not limited to multiple-use or single-use with a multiple device configuration, such as a stack.

FIGS. 10a, 10b, and 10c depict the structure and operational steps of one embodiment of the fluid access interface of the present invention. The fluid access interface 1000 is employed to access a fluid sample, present in a main fluid line connected to a patient or any other form of tubing. In one embodiment, the fluid access interface 1000 accesses the fluid sample from a dual-sided needle-less access port or seal 1004 attached to the main fluid line 1001 via shuttle 1003 and delivers the fluid sample to a test substrate [not shown].

Referring to FIG. 10a, apparatus 1000 is used to transfer a fluid sample from main fluid line 1001 to test substrate 1002. Shuttle device 1003 is employed to penetrate first membrane 1004a of the dual-sided needle-less port or seal 1004 and access fluid. As shown in FIG. 10b, shuttle device 1003 passes into first membrane 1004a of dual-sided needle-less port or seal 1004 and collects a fluid sample. Shuttle device 1003 then passes through second membrane 1004b of dual-sided needle-less port or seal 1004 and delivers the sample to test substrate 1002, as shown in FIG. 10c. Shuttle device 1003 is a single-use device employed to facilitate a sanitary and uncontaminated fluid sample without passing back through the sample port.

FIGS. 11a and 11b illustrate the structure and operational steps of another embodiment of the fluid access interface of the present invention wherein an air jet fluid access port is employed. The fluid access interface is used to access a fluid sample, present in a main fluid line connected to a patient or any other form of tubing. In one embodiment, the fluid access interface 1100 accesses the fluid sample from an air jet fluid access port attached to the main fluid line and delivers the fluid sample to a test substrate. Fluid access interface device 1100 comprises valve 1103 used to remove a volume of fluid from the main fluid line 1101 through an exit port 1107 to a substrate 1102. Valve 1103 rotates from a first state, shown in FIG. 11a, to a second state, shown in FIG. 11b, which aligns a collected sample with exit port 1107 and air pump inlet 1109. A low volume air pump 1104 then pushes the fluid sample through the inlet 1109 onto the test substrate 1102, as shown in FIG. 11b. A micro-filter 1105 is preferably employed to ensure that no contamination enters the system or the fluid sample. Valve 1103 then returns to the first state from the second state after disbursing the blood sample on substrate 1102.

Figure 12A:
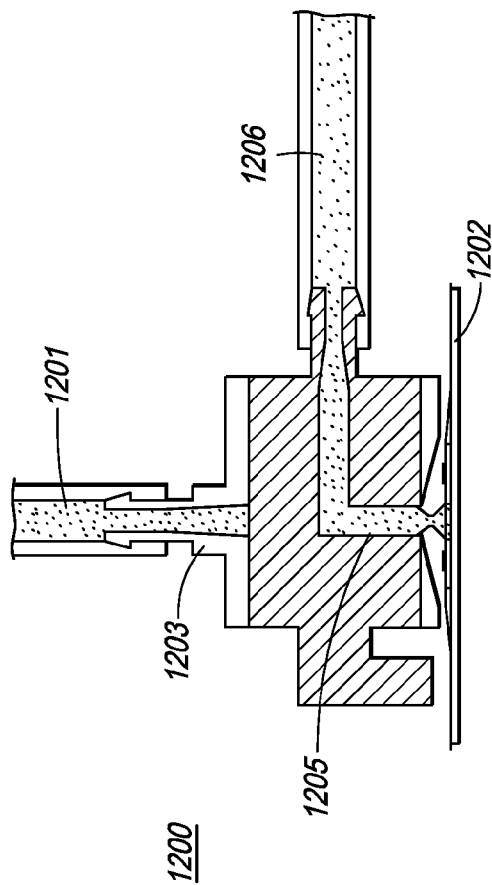
FIGS. 12A and 12B depict the structure and operational steps of one embodiment of the fluid access interface of the present invention wherein a distribution valve is employed.
Figure 12B:
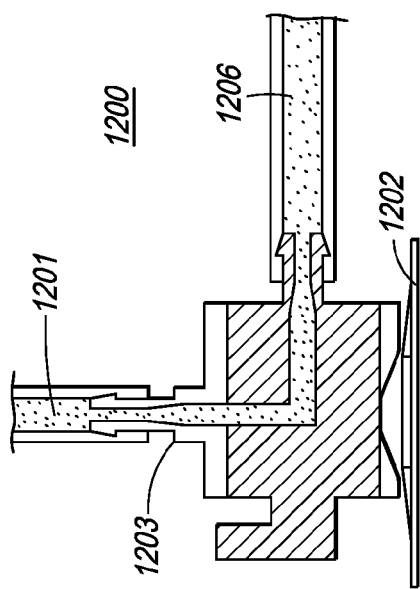

FIGS. 12a and 12b depict the structure and operational steps of another embodiment of the fluid access interface of the present invention wherein a distribution valve is used. The fluid access interface is employed to access a fluid sample, present in a main fluid line connected to a patient or any other form of tubing. Fluid access interface 1200 accesses the fluid sample from the main fluid line 1201 and delivers the fluid sample to a test substrate 1202. As shown in FIG. 12a, device 1200 comprises a by-pass distribution valve 1203, employed to access fluid from main fluid access line 1201 and deliver it to test substrate 1202. Valve 1203 is used to divert fluid flow to a side path 1205, as shown in FIG. 12b. The fluid sample is then pushed onto the test substrate 1202 via the side path with a pump (not shown).

FIGS. 13a and 13b illustrate the structure and operational steps of another embodiment of the fluid access interface of the present invention wherein the distribution valve shown in FIG. 12 is further equipped with a sterile filter. The operational steps are similar to those described in detail with respect to FIG. 12. The details will only be described herein where necessary to differentiate this embodiment from that described with respect to FIG. 12.

Referring now to FIG. 13a, device 1300 is employed to access fluid from main fluid line 1301 and deliver the fluid sample to test substrate 1302. Valve 1303 is used to divert the flow of fluid from main fluid line 1301 to a side path 1305. Pump [not shown] is then used to push the fluid sample onto a test substrate 1302. Valve 1303 also contains an opening 1307, where the fluid sample exits to contact the test substrate 1302. At opening 1307, device 1300 further comprises micro-filter 1308 through which the fluid sample passes prior to coming into contact with test substrate 1302. Micro-filter 1308 serves to protect the fluid inside valve 1303 from contamination. FIG. 13b illustrates the fluid sample coming into contact with the test substrate 1302. In one embodiment, micro-filter 1308 is cleaned via purging clean fluid (not blood) before and after sample collection onto a "purge pad" (not shown) for disposal. The micro-filter 1308 is cleaned when the valve 1303 is rotated back to "by-pass flow" position.

Figure 14A:
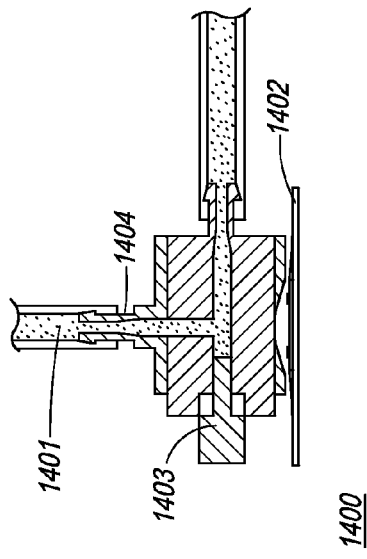
FIGS. 14A, 14B, 14C, and 14D depict the structure and operational steps of one embodiment of the fluid access interface of the present invention implemented as a distribution valve with an integrated dispensing pump.
Figure 14B:
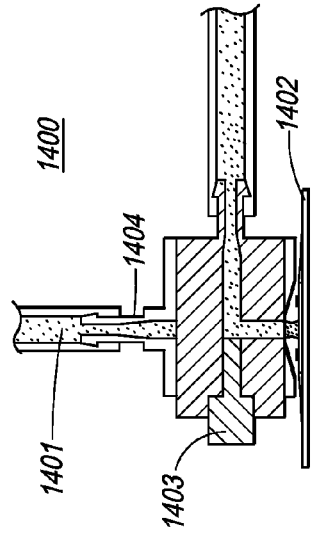
Figure 14C:
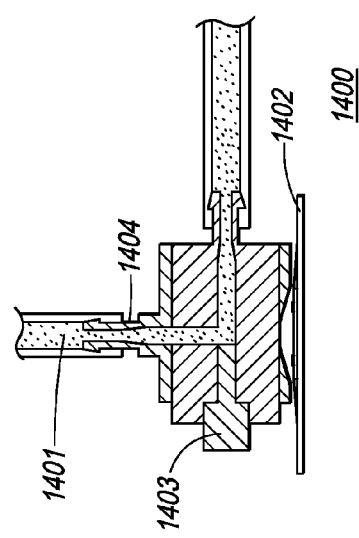
Figure 14D:
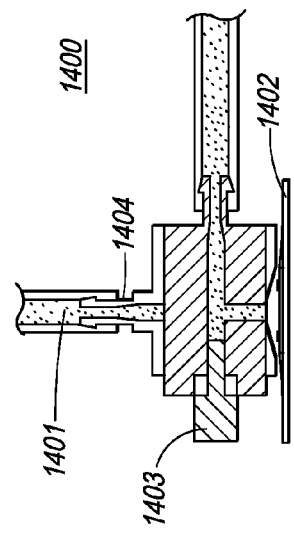

FIGS. 14a, 14b, 14c, and 14d depict the structure and operational steps of one embodiment of the fluid access interface of the present invention employing a distribution valve, such as that shown in FIGS. 12 and 13, further equipped with an integrated dispensing pump. As shown in FIG. 14a, device 1400 is used to access fluid from a main fluid line 1401 and deliver the fluid sample to a test substrate 1402. As shown in FIG. 14b, plunger 1403 on an internal pump (not shown) is pulled to obtain a fluid sample. Valve 1404 is rotated to divert the main flow of fluid to a side path, as shown in FIG. 14c. The fluid sample is subsequently pushed onto the test substrate 1402 with plunger 1403, as depicted in FIG. 14d.

Figure 15:
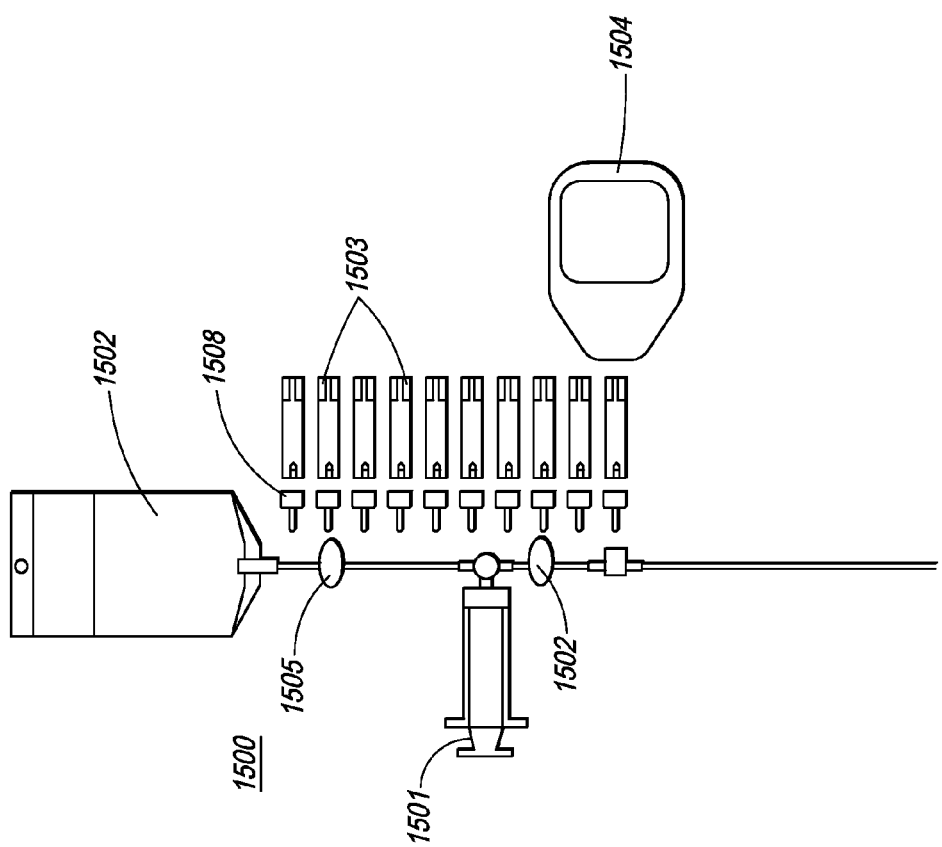
FIG. 15 is a schematic diagram of an exemplary embodiment of an automated blood parameter testing apparatus for use with the present invention.

FIG. 15 illustrates one embodiment of an exemplary automated blood parameter testing apparatus for use with the fluid access interface of the present invention. U.S. patent application Ser. No. 11/157,110, assigned to Applicant, is herein incorporated by reference. The invention therein is directed towards an automated blood parameter testing apparatus in which a blood parameter measurement element is employed.

As shown in FIG. 15, in one exemplary embodiment, the various embodiments of the fluid access interface of the present invention are used with an automated blood parameter testing apparatus 1500. In one embodiment, the automated blood parameter testing apparatus is a glucose meter 1504. In another embodiment, the blood parameter testing apparatus 1500 is used with any one of the fluid access interfaces 1508 disclosed herein. In one embodiment, a glucose testing strip 1503 is in fluid communication with the fluid access interface 1508. The fluid is moved from infusion bag 1502 into a patient [not shown] and blood samples are retrieved from a patient using a pump 1501, preferably a syringe pump. A plurality of valves 1505 may be used to control fluid flow from either the infusion bag 1502 or patient [not shown]. The automated device 1500 is programmable to initiate a sample reading periodically or via operator input. Operator input is initiated by, but not limited to, the push of a button. In addition, operator input may be initiated at the central monitoring station.

Figure 16:
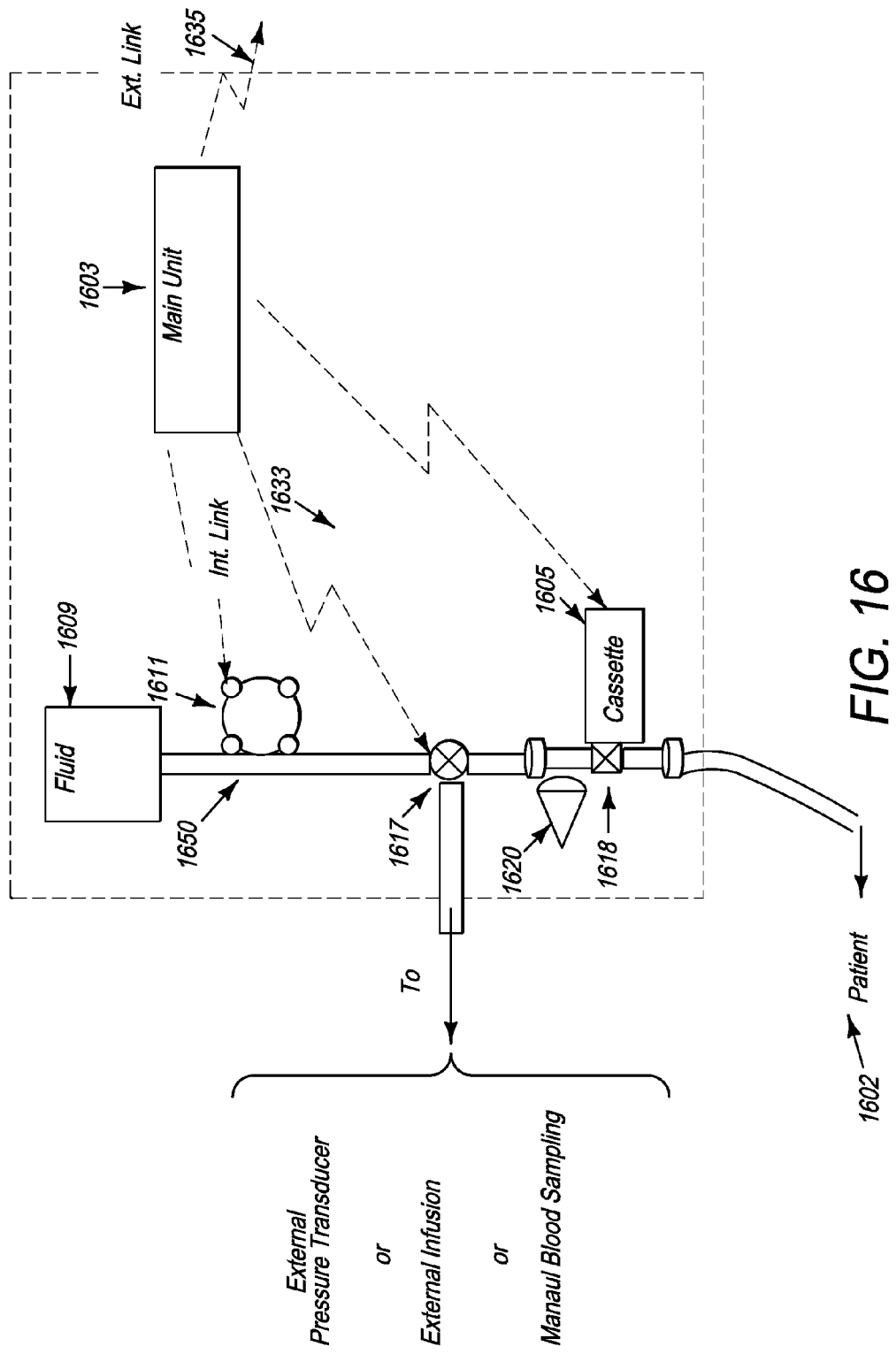
FIG. 16 is a schematic diagram of another exemplary embodiment of an automated blood parameter testing apparatus for use with the present invention.

FIG. 16 illustrates another embodiment of an exemplary automated blood parameter testing apparatus for use with the fluid access interface of the present invention. U.S. patent application Ser. No. 11/048,108, assigned to Applicant, is herein incorporated by reference. The invention therein is directed towards an automated blood parameter testing apparatus in which a blood parameter measurement element is employed.

As shown in FIG. 16, in one exemplary embodiment, the various embodiments of the fluid access interface of the present invention are used with an automated blood parameter testing apparatus 1600. It is to be understood that such embodiment is exemplary, but not limiting, and that the automated blood analysis device 1600 may be connected to other external devices at the same vascular access point. Automated blood analysis device 1600 blocks the operation of any connected infusion and/or external device (such as an external pressure transducer) during the period of blood sampling, in order to ensure that the blood sample is not diluted/altered by other fluids injected in the patient.

During normal operation, pump 1611 drives fluid from infusion bag 1609 through a main line 1650 and into the patient 1602. A first stopcock 1617 blocks fluid from traveling out of the main line 1650 and is periodically opened to permit an external infusion, manual blood sampling, or the measurement of pressure using an external transducer.

When performing automated blood sampling and measurement of required blood analytes, main unit 1603 directs pump 1611 to reverse, thereby reversing the flow of fluid. Main unit 1603 communicates with the valve 1617, pump 1611, and sensor cassette 1605 using internal links 1633 which can be wired or wireless. It further communicates to external monitoring stations using external link 1635. Once the pump 1611 reverses operation, blood is pulled from patient 1602 into the main line 1650. The blood is drawn along the tube until the remaining infusion volume and the initially diluted blood volume passes fluid access interface 1618 which is proximate to sensor cassette 1605. A pressure measurement element can be used to ensure pressure does not increase excessively.

Main unit 1603 calculates the required volume of blood to be withdrawn based on the diameter and length of the tubing and according to a programmable dead-space volume, which can be either pre-calibrated or user-defined. Optionally, a blood presence sensor 1620 can be used to establish whether undiluted blood has reached the tube segment proximal to the fluid access interface 1618. When undiluted blood reaches the fluid access interface 1618, the fluid access interface is activated to obtain an undiluted blood sample for measurement by the sensor cassette 5. The fluid access interfaces disclosed herein may be used obtain the undiluted blood samples.

When the undiluted blood sample is taken inside sensor cassette 1605 (by fluid access interface mechanism 1618), a sensor (from a plurality of sensors within sensor cassette 1605) is placed into contact with the drawn blood sample. Sensor is preferably, but not limited to, a single use sensor, and is used to measure patient blood analyte(s) and blood parameter(s). Sensor is preferably a component of a manual test device, such as, but not limited to glucose test strips for measuring glucose levels.

While the blood sample is analyzed, blood withdrawal from patient 1602 is stopped and main unit 1603 reverses the operation of pump 1611. The tubing components, including line 1650, are then flushed by purging fluid from fluid bag 1609. The remaining blood in line 1650 may be infused back into patient 1602.

Single use sensors are preferably packaged into disposable cassette 1605 and replaced periodically. Sensor cassette 1605 is preferably sterile, and is also preferably disposed after use with a single patient 1602. Sensor cassette 1605 supports at least one or a plurality of single use sensors that are advanced sequentially and positioned for direct contact with the drawn blood sample. After completing a measurement, the used sensor is automatically advanced from the measurement location to a location for disposed sensors. Between measurements, the system moves a new sensor forward into contact with fluid access interface 1618, thus replacing the one used in the previous measurement. Various cassette sizes can be manufactured and sensor cassette 1605 can be available, but is not limited to 25, 50, or 100 measurement capacities. In one design, sensor cassette 1605 also stores the consumed test supplies and sample waster.

The use of single-use sensors (similar to the use of finger stick sensors) eliminates the need for time-consuming operator-directed calibration procedures. In particular, each sensor cassette 1605 can be factory pre-calibrated. Optionally, sensor cassette 1605 or plurality thereof and individual sensors 1619 of the same type have the same pre-calibration values. Main display and control unit 1603 can automatically read the cassette factory calibration values by standard means well-known to those of ordinary skill in the art, such as by reading the data from a barcode or an EPROM embedded in sensor cassette 1605. Optionally, factory values may be entered manually.

In addition, sensor cassette 1605 may be hermetically sealed and/or include humidity controls means, such as, but not limited to a small bag of dessicant material. In another option, each sensor or a portion thereof, may be contained in a packaging that is automatically opened prior to measurement. Optionally, the measurement portion of the sensors can be covered with a thin layer that protects the reagent area against moisture and/or light during storage (particularly useful for both electrochemical and optochemical sensors). The thin protective layer can be automatically peeled off by a peeling element (not shown), prior to the sensor being placed in position for measurement. The peeling element may comprise, but is not limited to, an edge-knife element strategically placed inside sensor cassette 1605.

When using electrochemical sensors, sensor cassette 1605 includes an electronic interface to main unit 1603 of automated blood analysis device 1600. When using optochemical or optical sensors, an electronic interface is optional, and sensor cassette 1605 can be designed to work with only a opto-mechanical interface to main unit 1603. In another embodiment, sensor cassette 1605 may optionally include a small battery power supply in case of power failure.

In one embodiment, sensor cassette 1605 may be either attached or inserted into main unit 1603. In the alternative, main unit 1603 may include an external sub-unit (not shown) that serves as the receiving interface for sensor cassette 1605. Thus, sensor cassette 1605 can be placed in proximity to patient 1602 without limiting the size of main unit 1603. In another embodiment, sensor cassette 1605 may optionally be attached to main unit 1603 by means of a data connector, an optional power connection means, and tubing.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention is not to be limited to the details given herein, but may be modified within the scope of the appended claims.

We claim:

1. A blood constituent measuring device comprising:
   at least one fluid access interface configured to automatically interface with a patient blood access line at a sampling port to access a blood sample therefrom and to separate the blood sample from the patient blood access line, said at least one fluid access interface comprising a container configured to contain the blood sample separated from the patient blood access line;
   a plurality of test substrates, wherein the at least one fluid access interface is configured to transfer each of a plurality of blood samples to each of the plurality of test substrates, wherein the at least one fluid access interface comprises a plurality of fluid access interfaces wherein each fluid access interface is configured to transfer a blood sample to a corresponding test substrate of the plurality of test substrates; and at least one pump element configured to direct the separated blood sample to the corresponding test substrate.

2. The device of claim 1, wherein the at least one fluid access interface is movable with respect to the sample port.

3. The device of claim 1, wherein the device is configured to transfer the blood samples to the corresponding test substrates using a predetermined schedule.

4. The device of claim 1, further comprising a housing containing said plurality of test substrates.

5. The device of claim 1, further comprising an infusion source coupled to the patient blood access line.

6. The device of claim 1, wherein the at least one pump element comprises a flexible portion configured to direct the separated blood sample to the test substrate.

7. The device of claim 6, wherein the flexible portion is configured to contract.

8. The device of claim 7, wherein the flexible portion is configured to expand.

9. The device of claim 1, wherein the container comprises a tube.

10. The device of claim 1, wherein the container comprises a valve.

11. The device of claim 1, wherein the container comprises a cylinder.

12. The device of claim 1, wherein the test substrate comprises a glucose test substrate.

13. The device of claim 1, wherein the at least one pump element is further configured to pull the blood sample from the sampling port.

* * * * *